United States Patent [19]

Avar et al.

[11] Patent Number: 5,616,636

[45] Date of Patent: Apr. 1, 1997

[54] PHOSPHONITE-HALS AND PHOSPHITE-HALS COMPOUNDS AS STABILIZERS

[75] Inventors: Lajos Avar, Biel-Benken, Switzerland; Peter Staniek, Kandern, Germany; Klaus Stoll, Ruemmingen, Germany; Wolf D. Habicher; Uwe Hähner, both of Dresden, Germany

[73] Assignee: Sandoz Ltd., Basel, Switzerland

[21] Appl. No.: 396,050

[22] Filed: Feb. 27, 1995

Related U.S. Application Data

[63] Continuation of Ser. No. 206,813, Mar. 7, 1994, abandoned, which is a continuation of Ser. No. 28,855, Mar. 10, 1993, abandoned.

[30] Foreign Application Priority Data

| Mar. 11, 1992 | [GB] | United Kingdom | 9205308 |
| May 6, 1992 | [GB] | United Kingdom | 9209759 |
| Oct. 9, 1992 | [GB] | United Kingdom | 9221279 |
| Nov. 23, 1992 | [GB] | United Kingdom | 9224522 |

[51] Int. Cl.$^6$ .................. C08K 5/5393; C08K 5/529; C07F 9/576

[52] U.S. Cl. .................. 524/102; 524/100; 524/103; 546/22; 546/25

[58] Field of Search .................. 524/103, 100, 524/102, 99; 546/22, 25

[56] References Cited

U.S. PATENT DOCUMENTS

| 4,096,114 | 6/1978 | Minagawa | 260/45.8 |
| 4,210,576 | 7/1980 | DiBattista | 260/45.8 NE |
| 4,229,382 | 10/1980 | Mayer et al. | 260/930 |
| 4,259,492 | 3/1981 | Rasberger | 524/102 |
| 4,293,466 | 10/1981 | DiBattista | 260/45.8 N |
| 4,322,527 | 3/1982 | Rasberger | 524/102 |
| 4,396,735 | 8/1983 | Minagawa et al. | 524/102 |
| 4,434,109 | 2/1984 | Rasberger | 260/958 |
| 4,542,199 | 9/1985 | Kaminsky et al. | 526/160 |
| 4,579,682 | 4/1986 | Rasberger | 524/102 |
| 4,661,594 | 4/1987 | Rasberger et al. | 524/102 |
| 4,673,701 | 6/1987 | Minagawa | 524/99 |
| 4,752,597 | 6/1988 | Turner | 526/160 |
| 4,803,234 | 2/1989 | Cantatore et al. | 524/100 |
| 4,808,645 | 2/1989 | Ravichandran | 524/99 |
| 4,937,299 | 6/1990 | Ewen et al. | 526/119 |
| 5,021,481 | 6/1991 | Galbo et al. | 524/102 |
| 5,340,855 | 8/1994 | Meier et al. | 524/102 |
| 5,401,845 | 6/1994 | Pitteloud et al. | 546/25 |
| 5,405,891 | 4/1995 | Pitteloud | 524/102 |
| 5,422,067 | 8/1995 | Pitteloud | 546/25 |

FOREIGN PATENT DOCUMENTS

| 0232224 | 8/1987 | European Pat. Off. . |
| 0389430A1 | 9/1990 | European Pat. Off. . |
| 2811667 | 9/1979 | Germany . |
| 3928291 | 2/1991 | Germany . |
| 01-186898 | 7/1989 | Japan . |
| 2227490 | 8/1990 | United Kingdom . |
| 0389430 | 9/1990 | United Kingdom . |
| 2247241 | 2/1992 | United Kingdom . |
| 2252325 | 8/1992 | United Kingdom . |

*Primary Examiner*—Veronica P. Hoke
*Attorney, Agent, or Firm*—Robert S. Honor; Carl W. Battle; Gabriel Lopez

[57] ABSTRACT

A composition comprising:
  a) a compound containing a phosphite or phosphonite group and at least one 2,2,6,6-tetraalkylpiperidinyl group, and
  b) a polyolefin which has been produced in the presence of a catalyst which is either
  i) a supported Zeigler catalyst or
  ii) a metallocene catalyst,
from which polyolefin the catalyst has not been removed.

8 Claims, No Drawings

PHOSPHONITE-HALS AND PHOSPHITE-HALS COMPOUNDS AS STABILIZERS

This is a continuation application of application Ser. No. 08/206,813 filed on 07 Mar. 1994, which in turn is a continuation application of application Ser. No. 08/028,855 filed on 10 Mar. 1993 all now abandoned.

The invention relates to the use of certain compounds which may act as processing stabilizers and simultaneously act as light stabilizers in polyurethanes and polyolefins (including polyalkenes) that have been made with a II and above Generation catalyst (e.g. II to V Generation catalysts).

According to the invention, there is provided a polymer composition comprising:

a) a compound containing a phosphite or phosphonite group and at least one (preferably 1 to 4) 2,2,6,6-tetraalkylpiperidinyl groups (hereinafter defined as "component a"), and b) a polyolefin which has been produced in the presence of a catalyst which is either
  i) a supported Ziegler catalyst or
  ii) a metallocene catalyst,
from which polyolefin the catalyst has not been removed (hereinafter "component b").

Further according to the invention, there is provided a polymer composition comprising a polyurethane or resins capable of forming a polyurethane and a) a compound containing a phosphite or phosphonite group and at least one (preferably 1 to 4) 2,2,6,6-tetraalkylpiperidinyl groups (hereinafter defined as component a).

Still further according to the invention, there is provided a coating composition in powder form comprising a polymeric powder coating material to which is applied a compound containing a phosphite or phosphonite group and at least one (preferably 1–4) 2,2,6,6-tetraalkylpiperidinyl group (herein defined as component a).

The term "metallocene" is used to describe new catalysts of Generation V and above which are used in the production of polyolefins (especially polyethylenes and polypropylenes) as described, for example, in "Modern Plastics" 10/91 p. 46–49 or in "Makromolekulare Chemie" 192 (1991) 1059–1065.

The supported Ziegler catalysts carriers (such as those supported on a halogen-containing magnesium compound) are well known and are described in Table 1 below.

Preferably component a) is present in an amount of 0.01–5%, more preferably 0.05–2% based on the weight of polymer material (such as polyolefin, polyurethane (or resins capable of forming polyurethane) or polymeric powder coating material present in the composition.

Preferably component a) is a compound of formula I

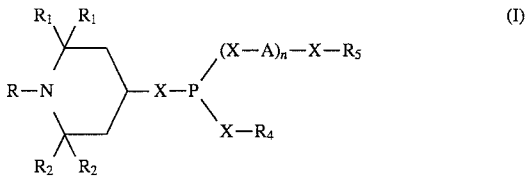

in which

R is hydrogen; oxygen; —OH; $C_{1-24}$alkyl; —O—$C_{1-24}$alkyl; —O—CO—$C_{1-24}$alkyl; —O—CO-phenyl or —$COR_{15}$; where $R_{15}$ is —$C(R_3)$=$CH_2$, $C_{1-6}$alkyl, phenyl, CO—$C_{1-24}$alkyl, —CO-phenyl, —$NR_7R_8$, —$CH_2$—$C_6H_5$, —CO—$OC_{1-12}$alkyl or —COOH; $R_3$ is hydrogen or $C_{1-4}$alkyl; $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$, independently, is —$CH_3$ or —$CH_2(C_{1-4}$alkyl) or both groups $R_1$ form a group —$(CH_2)_5$—;

each $R_2$, independently, is —$CH_3$ or —$CH_2(C_{1-4}$alkyl) or both groups $R_2$ from a group —$(CH_2)_5$—;

each of $R_4$ and $R_5$, independently, is selected from methyl, ethyl, linear or branched $C_{3-24}$alkyl, $C_{7-24}$alkaryl, $C_{5-24}$aralkyl, $C_{6-24}$cycloalkyl, $C_{6-24}$aryl and the groups of formula a) and b)

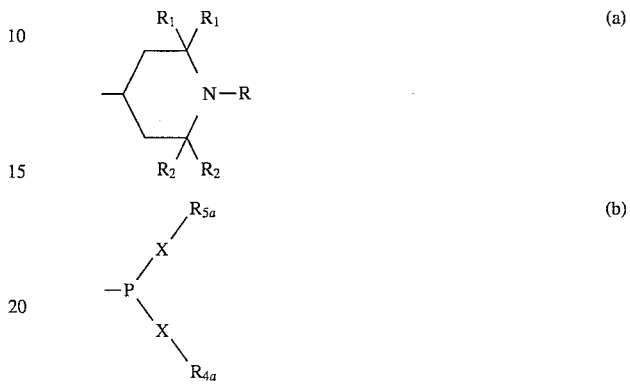

provided only one of $R_4$ and $R_5$ is a group of formula b); or both groups $R_4$ and $R_5$ together form a group of formula c);

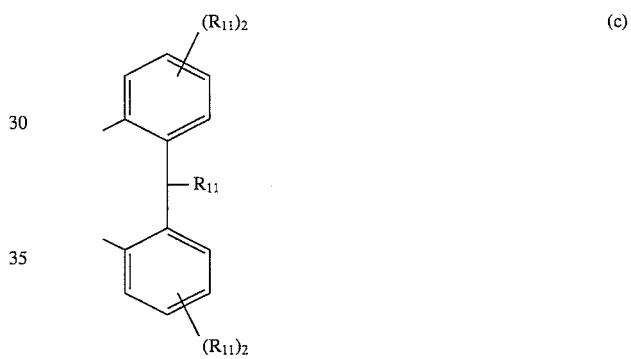

in which $R_{4a}$ and $R_{5a}$, independently, are selected from —$R_{10}$, and a group of formula a); where $R_{10}$ is methyl, ethyl, linear or branched $C_{3-24}$alkyl, $C_{5-24}$cloalkyl, $C_{7-24}$alkaryl, $C_{7-24}$ aralkyl or $C_{6-24}$aryl;

A is $C_{1-24}$alkylene, $C_{6-24}$cycloalkylene, $C_{6-24}$arylene (preferably phenylene), $C_{7-24}$aralkylene or a group of formula d)

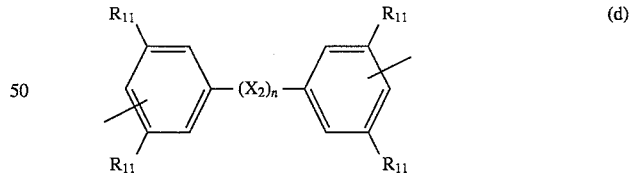

where n=0 or 1;

each $R_{11}$, independently, has a significance of $R_{10}$ or is hydrogen;

$X_2$ is a direct bond, —$NR_3$—, —O—, —S— or $C_{1-24}$alkylene [especially $C_{1-4}$alkylene (e.g. —$(CH_2)_{1-4}$—)] $C_{6-24}$cycloalkylene, $C_{6-24}$arylene (preferably phenylene), $C_{7-24}$alkarylene and $C_{7-24}$aralkylene, and each X, independently, is a direct bond, —$N(R_3)$—, —O—, or —S—; (preferably a direct bond or —O—).

Preferably $R_{11}$ is $R_{11}$', where R' is hydrogen or $C_{1-8}$alkyl, more preferably $R_{11}$", where $R_{11}$" is hydrogen, methyl, t-butyl or t-octyl.

R is preferably R' where R' is hydrogen, —O—CO-phenyl, $C_{1-18}$alkyl, $C_{1-18}$alkoxy, —CO—$R_{15}$' or —CO—

$CH=CH_2$ where $R_{15}'$ is $C_{1-8}$alkyl, $-CO-C_{1-8}$alkyl or $-CO-O-C_{1-4}$alkyl.

Preferably each $R_1$ is methyl and each $R_2$ is methyl.

A is preferably A' where A' is $C_{1-8}$alkylene, $C_{6-8}$cycloalkylene, $C_{6-12}$arylene or a group of formula d'

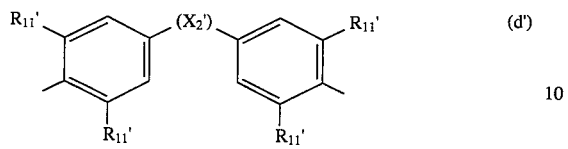

in which each $R_{11}'$ independently is hydrogen or $C_{1-8}$alkyl; and $X_2'$ is $C_{1-12}$alkylene, $C_{6-12}$arylene, $-O-$ or $-S-$.

Preferably in this Specification any aryl group is phenyl and any arylene group is phenylene unless indicated to the contrary.

Preferred compounds of formula I are selected from compounds of formula II to VII

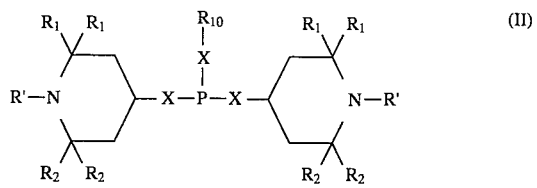

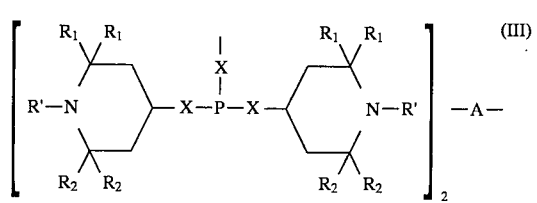

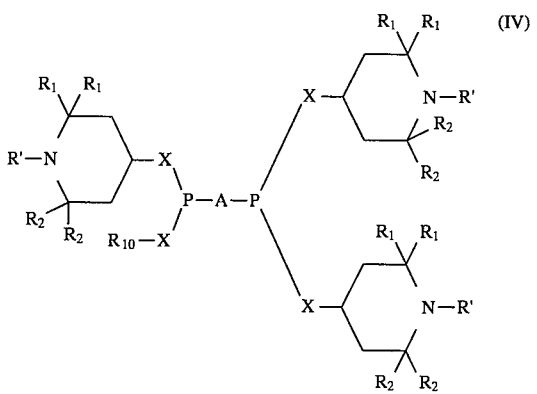

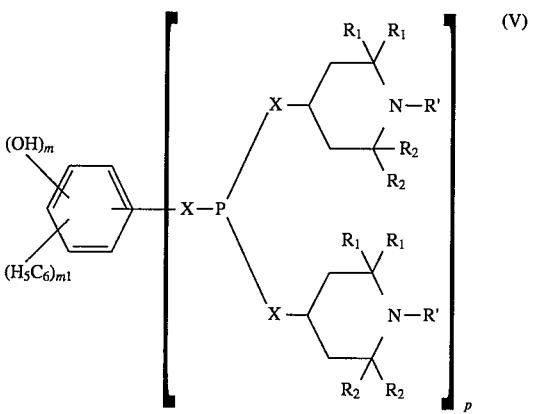

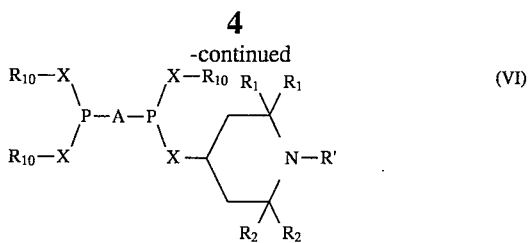

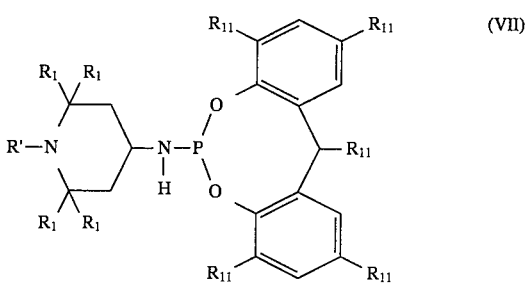

and mixtures thereof, where each m is 0 or 1, $m_1$ is 0 or 1 and p is 1, 2 or 3 and the other symbols are as defined above.

Compounds of formula II, where $R_{10}$ is other than phenyl and the X connected to $R_{10}$ is a direct bond, are new.

Compounds of formula V when m=1 and compounds of formula III where X is a direct bond are new. Compounds of formula V where m is 1, A is a group of formula d where $X_2$ is $C_{1-12}$alkylidene and at least one group $R_{11}$ is not H, are new.

Preferred compounds of formula I are of formula II or III, more preferably II.

Preferably each X attached to a tetraalkylpiperidinyl group is $-O-$.

Preferably in the group $-X-R_{10}$ X is a direct bond or $-O-$.

Preferably $R_{10}$ is $R_{10}'$ where $R_{10}'$ is $C_{1-8}$alkyl, $C_{5-12}$cycloalkyl, $C_{6-12}$aryl, $C_{7-24}$aralkyl or $C_{7-24}$alkaryl, more preferably $R_{10}''$ where $R_{10}''$ is $C_{1-8}$alkyl, $C_{5-12}$cycloalkyl, $C_{7-24}$aralkyl or $C_{7-24}$alkaryl.

More preferred compounds of formula III are of formula XIV and 3.

More preferred compounds of formula V are of formula XIII below.

More preferred compounds of formula I are of formula 1 to 9 below:

1. (2,6-Di-t-butyl-4-methyl-phenyl)-bis(2,2,6,6-tetramethylpipeddinyl) phosphite

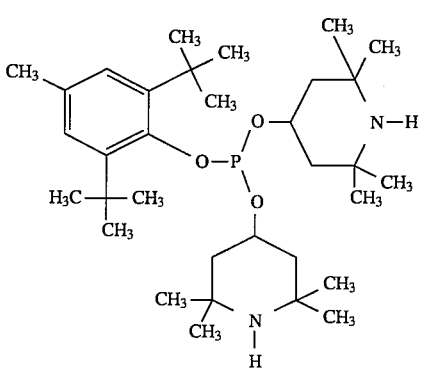

2. (2,6-Di-t-butyl-4-methyl-phenyl)-bis(N-methyl-2,2,6,6-tetramethylpiperidinyl)phosphite
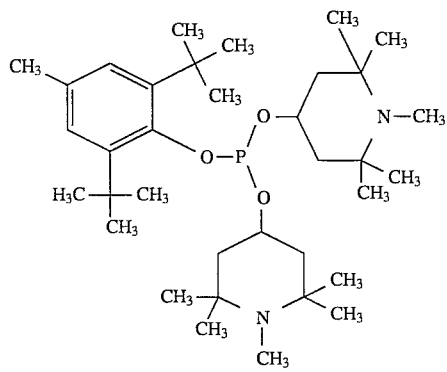
3. Tetrakis(N-methyl-2,2,6,6-tetramethylpiperidinyl)-4,4'-(3,3'5,5'-tetra-t-butyl-phenyl) methane)-diphosphite
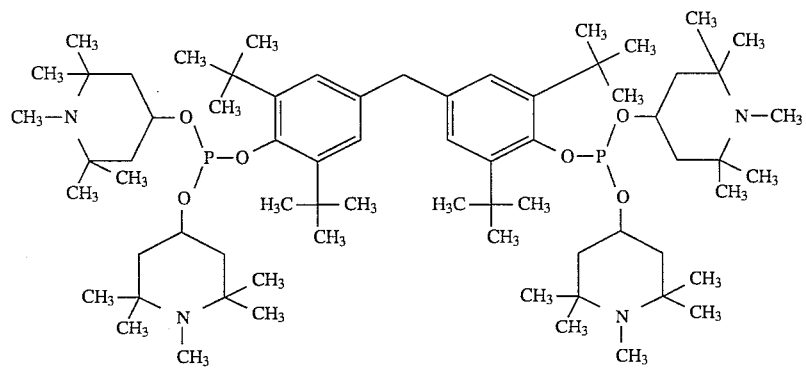
4. Bis(2,2,6,6-tetramethylpiperidinyl)-phenyl-phosphonite
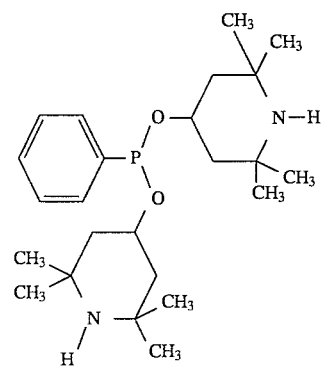
5. Bis(N-methyl-2,2,6,6-tetramethylpiperidinyl)-phenyl-phosphonite
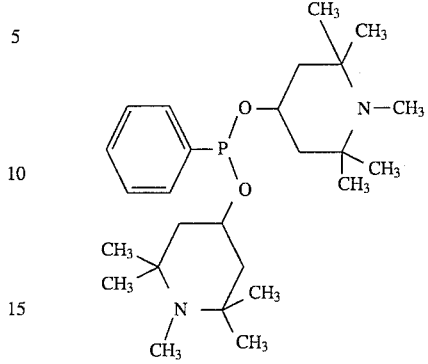
6. Bis(2,2,6,6-tetramethylpiperidinyl)biphen-4-yl-phosphonite, and
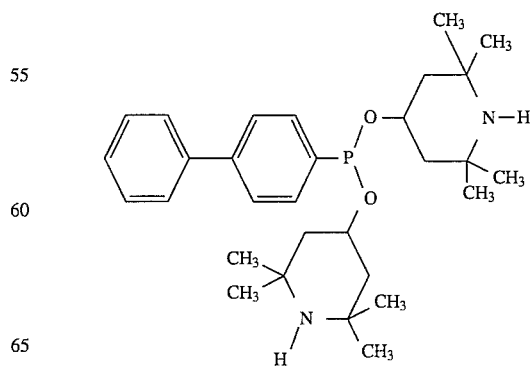

7. Bis(N-methyl 2,2,6,6-tetramethylpipeddinyl)-biphen-4-yl-phosphonite

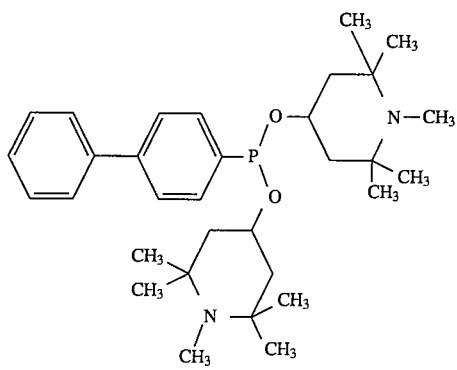

8. (2,4,6-tri-t-butyl-phenyl)-bis(2,2,6,6-tetramethylpipeddinyl) phosphite

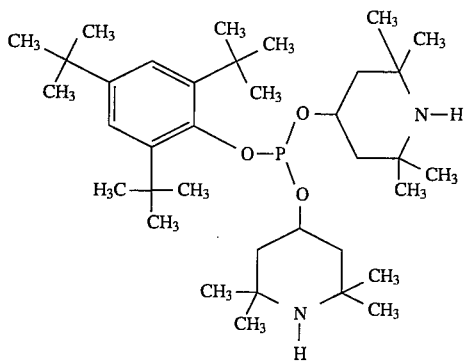

9. (2,4,6-tri-t-butyl-phenyl)-bis(N-methyl-2,2,6,6-tetramethylpiperidinyl)phosphite

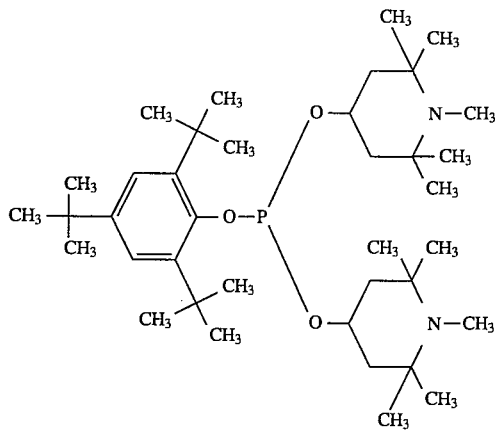

Component a) may also be a mixture comprising
i) 1–90% of a phosphonite of formula I (preferably a compound of formula II to VII) hereinafter defined as component i); and ii) 99–10% of a phosphite of formula VIII (hereinafter defined as component ii)

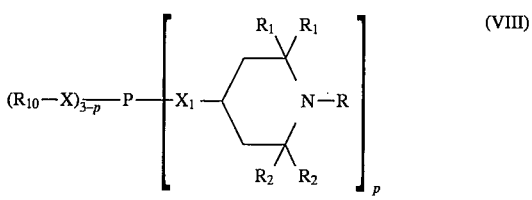

where p is 1, 2, or 3, $X_1$ is —O— or —$NR_3$ and the other symbols are as defined above.

Compounds of formula I can be prepared by reacting one mol of a compound of formula X

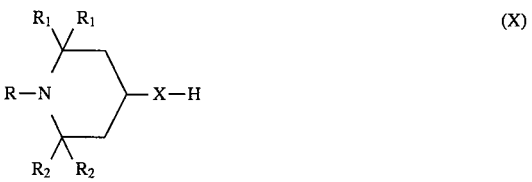

with one mol of a compound of formula XI

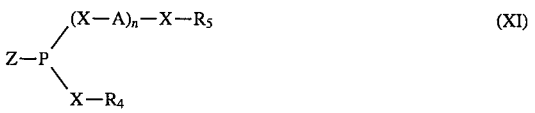

or by reacting 2 mols of a compound of formula X with 1 mol of a compound of formula XII

where Z is Cl, Br or $N(R_7)_2$

Further, the compounds of formula I to VII can be made by other known methods from known compounds.

Further according to the invention, there is provided a compound of formula XIII

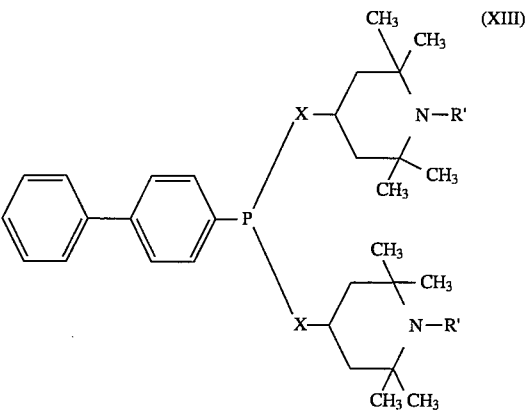

in which the symbols are as defined above. Preferably in the compounds of formula XIII R' is R" where R" is hydrogen or $C_{1-4}$alkyl.

Further according to the invention there is provided a compound of formula XIV

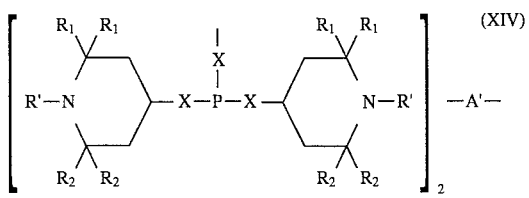

in which the symbols are as defined above.

Preferred polymeric materials which can be stabilized are polyolefins such as polypropylene, polyethylene (e.g. high density polyethylene, low density polyethylene, linear low density polyethylene or medium density polyethylene) and polyalkenes and copolymers thereof. Preferred polyalkenes include polypentenes and polybutenes e.g. poly-4- methylpentene, poly-3-methylpentene and 3-methylpentene and 3-methyl-butene-1.

Preferred polyurethanes are those prepared from isocyanate resins and polyols. Preferred isocyanates are those commercially available as Desmodur, Elastan, Lupranat, Tedimon, Scuranat, Suprasec, Systanat, Hylene, Isonate (-Papi), Multrathane, Nacconate and Sumidur.

Preferred polyols are those commercially available as Desmophen, Lupranol, Lupraphen, Glendion, Napiol, Scuranol, Caradol, Daltolac, Daltorez, Diorez, Estolan, Propylan, Arinol, Bermodol, Isonol, Metpol, Multron, Multranol, Niax Polyol, Pluracol, Quadrol, Thanol, Voranol and Sumiphen.

Such polyurethanes are as describes in Saechtling: Kunststoff Taschenbuch 23 Ausgabe-published by Cad Hansen Verlag 1986 (esp. p. 339–410). The contents of this book are incorporated herein by reference.

The new stabilizer compositions are especially suitable for use in polyolefins and especially α-polyolefins prepared using processing catalysts known as Generation II to Generation V catalysts and which have not been subjected to a catalyst removal step. By the term "catalyst removal step" used herein is meant a step for the purpose of positively removing the catalyst residues contained in the polymerized polyolefins or treating the polyolefins with the compound, such as an alcohol or water, which can react with the catalyst residue and inactivate or solubilize the residue, and then removing the inactivated or solubilized catalyst residue by physical means such as filtration, washing and centrifuging. Thus, in the case of suspension polymerization, the step of separating the resulting polymer from a dispersion medium, such as a solvent or a liquefied monomer, does not fall under the above-mentioned definition of the catalyst residue removal step, although the catalyst dissolved in the dispersion medium may be removed by a separation step. The step of adding a small amount of catalyst poisons such as ethers, alcohols, ketones, esters and water to the resulting polymer, to inactivate the catalyst remaining after the completion of polymerization, or the step of treating the resulting polymer suspension with gas such as steam or nitrogen to remove the dispersion medium also does not fall under the above-mentioned definition of the "catalyst residue-removal" step.

What we mean by Generation I catalysts are titanium halide catalysts and an organo aluminium compound or an organo aluminium halide.

What we mean by Generation II catalysts are Generation I catalysts supported on an organo-magnesium compound or based on an organo chromium compound supported on $SiO_2$.

What we mean by a Generation III catalyst is a Ziegler type complex catalyst supported on a halogen-containing magnesium compound.

What we mean by a Generation. IV catalyst is a Generation III catalyst with a silane donor.

What we mean by Generation V catalysts is a bis-indenyl organo titanium compound supported on alumoxane or bis cyclopentadienyl titanium halides activated by aluminium alkyl compound.

Further generations of highly specific catalysts, especially useful for manufacturing highly stereoregular poly-α-olefins, which are presently under development, belong in the sense of the present invention also to the aforementioned generations of supported catalyst systems. Examples for the microstructure of such highly stereoregular polyolefins are given by syndiotactic polypropylene, isotactic stereoblock polymers, isotactic polypropylene containing steric defects randomly distributed along the polymer chain (so-called anisotactic polypropylene) or stereoirregular stereoblock polymers. Due to the rapid progress in the development of newer generation catalyst systems the commercial significance of these polymers with novel, highly interesting properties increases more and more. However, residues of such further catalyst generations, as long as they contain metals of the 3d, 4d and 5d series of the periodic system supported analogously to the earlier catalyst generations, can also cause disadvantageous properties in the polymer, so long as such residues are still present in the polymer even if in a deactivated form. Because of this, it can therefore be expected that the new compositions according to the invention are also suitable for overcoming such disadvantageous properties of the polymer. This means that any disadvantageous interaction between processing stabilizers and the aforementioned residues of catalysts of further generations, particularly the hydrolysis of phosphites and phosphonites, is most effectively inhibited.

These generations of catalysts are described in the Twelfth Annual International Conference on Advances in the stabilization and Controlled Degradation of Polymers held in Luzern, Switzerland, 21–23 May 1990 in an article on pages 181 to 196 inclusive by Rolf Mülhaupt entitled "New Trends in Polyolefin Catalysts and Influence on Polymer Stability". The contents of this article is incorporated herein by reference and especially Table I on page 184 describing the Generation of Catalysts:

TABLE I

| | | Polyolefin Catalyst Evolution | | | |
|---|---|---|---|---|---|
| | Generation Example | Cat. Act. (gPP/gTi h atm) | % Act. Ti | Stereoreg. (% insol. in heptane) | Process Technology |
| I. | $TiCl_4/AlR_3$ | 40 | 0.01 | 45% | removal of cat. residues and atactic PP |
| | $TiCl_3/AlEt_2Cl$ | 30 | 0.1 | 92% | removal of catalyst residues |
| II | $Mg(OEt_2)/TiCl_4AlR_3$ | 40000 | | 50% | no removal of cat. residues |
| | $SiO_2/Cp_2Cr$ | 40000 | HDPE | | (mainly HDPE/LLDPE) |

TABLE I-continued

Polyolefin Catalyst Evolution

| Generation Example | Cat. Act. (gPP/gTi h atm) | % Act. Ti | Stereoreg. (% insol. in heptane) | Process Technology |
|---|---|---|---|---|
| III Mod. TiCl₃ cat. | 5000 | 1 | 95% | no purification |
| MgCl₂/TiCl₄/AlR₃ + ester donor | 20000 | 10 | 92% | |
| IV MgCl₂/TiCl₄/AlR₃ + silane donor | 40000 | 18 | 99% | no purification no extrusion |
| V Bis-indenyl-TiR₂ on (AlCH₃O)ₓ | 40000 | 100 | 99% | novel PPs, narrow MWD | in which R, in Table 1, is an organo group; HDPE is high density polyethylene, LLDPE is linear low density polyethyene, Cp is cyciopentadienyl, Et is ethyl, PP is polypropylene, MWD is molecular weight distribution and x is an integer above 2.

Further additives that can be added to a stabilizing or a polymeric composition according to the invention include antioxidants, such as sterically-hindered phenols, secondary aromatic amines or thioethers, such as described in "Kunststoff-Additive"- Gächter/Müller, Ed. 3, 1990 p. 42–50, the contents of which are incorporated herein by reference; acid scavengers such as sodium, magnesium or calcium stearates or lactates hydrotalcite or alkoxylated amines; U.V. stabilizers such as sterically hindered amines (for example N-unsubstituted, N-alkyl or N-acyl substituted 2,2,6,6-tetra-methylpiperidine compounds) [also know as hindered amine light stabilizers -HALS] and U.V. absorbers (e.g. 2-(2'-hydroxphenyl)-benztriazoles, 2-hydroxybenzophenones, 1,3-bis-(2'-hydroxybenzoyl)benzene salicylates, cinnamates and oxalic acid diamides), U.V. quenchers such as benzoates and substituted benzoates, antistatic agents, flameproofing agents, lubricants, plasticizers, nucleating agents, metal deactivators, biocides, impact modifiers, fillers, pigments and fungicides.

Stabilizing compositions according to the invention may be added to the polymeric material before, during or after the polymerization step and may be added in solid or molten form, in solution preferably as a liquid concentrate containing from 10 to 80% (more preferably 40 to 70%) by weight of the composition and 90 to 20% (more preferably 60 to 30%) by weight of a solid polymeric material which is identical with or compatible with the material to be stabilized.

The stabilizing compositions according to the invention may be incorporated by known methods into the polymeric material which is identical with or compatible with the material to be stabilized. Of particular importance is dry-blending of the compositions according to the invention with the polymer or coating shaped polymer particles, e.g. polymer spheres, with the present compositions in the form of a liquid, a solution or a suspension/dispersion.

Of particular importance is blending of the compounds with thermoplastic polymers in the melt, for example in a melt blender or during the formation of shaped articles, including films, tubes, fibers and foams by extrusion, injection molding, blow molding, spinning or wire coating.

The compounds of formula I of the invention are both good processing stabilizers and also good light stabilizers in polymeric materials, especially polyolefins.

Further, in this specification, where a range is given, the figures defining the range are included therein, Any group capable of being linear or branched is linear or branched unless indicated to the contrary.

Preferably the alkyl group in any 2,2,6,6-tetraalkylpiperidinyl group in this specification is-$CH_3$, —$CH_2(C_{1-4}alkyl)$, or both alkyl groups in the 2,2-position or both groups in the 6,6-position form a group —$(CH_2)_5$. More preferably the alkyl group is —$CH_3$.

In this specification preferably any $C_{1-24}$ alkyl group is a $C_{1-8}$aalkyl group, more preferably any $C_{1-8}$alkyl group is a $C_{1-4}$alkyl group, most preferably any $C_{1-4}$alkyl is methyl, ethyl or t-butyl and preferred alkoxy groups are methoxy or ethoxy.

For the avoidance of doubt, in this specification t-butyl means tertiary butyl, (—$C(CH_3)_3$).

Preferred powder coatings are described in "The Science of Powder Coatings - Chemistry, Formulation and Application"- David A. Bate published SITA - 1990, Vol. 1, the contents of which are incoporated herein by reference, especially pp. 249–277.

The powder coating compositions to which this invention can be applied are any powder coatings known in the art. The powders may be thermoplastic or thermosetting and include any known acrylic polyester, epoxy or urethane powder coatings commonly available. Particularly preferred powder coatings are based on acrylic powders and polyisocyanate resins.

Preferred powder coating are formulations based on epoxy resins for example DER 663 UE, HULS B68, Resiflow PU5, Ceriduol ACA8, Durcal 10 and Black Regal. Hydroxypolyester resins can be used in polyurethane powder coatings.

Powder lacquers are also described in U.S. Pat. No. 5,036,144, EP 299 420, U.S. Pat. No. 4 937 288 and JP 91-044588 the contents of which are incorporated herein by reference.

The invention will now be illustrated by the following Examples.

Example 1

Synthesis of biphenyl-bis(2,2,6,6-tetramethyl-pipefidinyl)-phosphonite

At ambient temperature and under inert conditions, 0.1 mol biphenyl-dichloro-phosphine is added dropwise to a suspension of 0.2 mol of 2,2,6,6-tetramethyl-piperidinol in 100 ml of triethylamine. After the addition has been completed, the mixture is refluxed for 5 hours. The product and the excess triethylamine are extracted twice with 50 ml toluene from the triethylamine hydrochloride at room temperature. From this solution the colorless product is precipitated by the addition of di-isopropyl-ether, filtered, washed with ether and dried in vacuo.

The yield is 56%, $\delta^{31}P$:155.5 ppm.

Example 2

A polymeric composition containing 100.0 parts of a 3rd generation polypropylene homopolymer (commerically available as Moplen FLS-20)

0.05 parts Irganox 1010, (tetrakis[methylene-3(3'5'-diter-t.butyl-4'hydroxyphenyl)-propionate]methane 0.1 parts calcium stearate, and 0.07 parts biphenyl-4,4'-bis(2,2,6,6-tetramethylpiperidinyl)-phosphonite is mixed by dry blender and extruded at 210° C. This composition is then multiple extruded in a Göttfert single screw extruder (270° C., d=20 mm, I:d=20, 50 min$^{-1}$ compression 1:3) and granulated after chilling the polymer melt in a water bath. The melt flow index (ASTM D-1238-70, 230° C., 2.16 kg) and the yellowness index (ASTM D-1925-70, on granules) are determined after the first, third and fifth passage.

Example 3

A polymeric composition is prepared as in example 2, except that 0.1 parts instead of 0.07 parts of biphenyl-4,4'-bis(2,2,6,6-tetramethyl-piperidinyl)-phosphonite are used.

Comparative example A:

A polymeric composition is prepared as in example 2, except that 0.07 parts of Irgafos 168 are used instead of 0.07 parts of biphenyl-4,4'-bis(2,2,6,6-tetramethyl-piperidinyl)-phosphonite.

Comparative example B:

A polymeric composition is prepared as in example 2, except that 0.1 parts of Irgafos 168 are used instead of 0.07 parts of biphenyl-4,4'-bis(2,2,6,6-tetramethyl-piperidinyl)-phosphonite.

| Example | MFI | | | YI | | |
|---|---|---|---|---|---|---|
| | 1. pass | 3. pass | 5. pass | 1. pass | 3. pass | 5. pass |
| Example 2 | 2.89 | 4.35 | 7.50 | −0.7 | −0.2 | 0.9 |
| Example 3 | 2.55 | 3.41 | 4.34 | −0.5 | 0.0 | 1.6 |
| Comp. ex. A | 3.22 | 5.04 | 6.89 | −1.3 | 1.1 | 3.0 |
| Comp. ex. B | 3.37 | 4.54 | 6.13 | −1.5 | 1.3 | 2.8 |

Example 4

A powder coating is made up from a hydroxy group containing acrylate and polyisocyanate. 2% of the compound 1 of Example 1 is added and conventionally worked into the coating by mixing, extruding, milling and sieving.

The powder coating is applied directly to primed metal panel by electrostatic spraying.

The resulting plates are exposed to a UVCON apparatus (UV fluorescent light 313 nm for 8 hours at 70° C. and 4 hours at 50° C.) to test for accelerated weathering.

Examples 5–9

By a method according to Example 2, polymeric compositions are prepared by mixing:

100.0 parts linear low density polyethylene (LLDPE, d=0.920g/cm$^3$)

0.02 parts Irganox 1010

0.10 parts calcium stearate 0.07 parts stabilizer as listed below by pre-extrusion at 170° C. and multiple extrusion at 240° C.

The following are the stabilizers used:

Example 5 phenyl-bis(1,2,2,6,6-pentamethylpiperidinyl)-phosphonite;

Example 6 biphenyl-bis(1,2,2,6,6-pentamethylpiperidinyl)-phosphonite;

Example 7 2,4-di-tert-butyl-phenyl-bis(1,2,2,6,6-pentamethylpiperidinyl)-phosphite;

Example 8 2,6-di-tert-butyl-4-methyl-phenyl-bis(1,2,2,6,6-pentamethylpiperidinyl)-phosphite;

Example 9 2,4,6-tri-tert-butyl-phenyl-bis(1,2,2,6,6-pentamethylpiperidinyl)-phosphite;

Comp. ex. C tris(2,4-di-tert-butyl-phenyl)phosphite (commercial processing stabilizer)

Comp. ex. D butanoic acid, polymer with 4-hydroxy-2,2,6,6-tetramethyl-1-piperidine-ethanol (commercial light stabilizer)

Comp. ex. E no additional stabilizer

The results can be seen in Table 2 below:

TABLE 2

| Example | MFI | | | YI | | |
|---|---|---|---|---|---|---|
| | 1. pass | 3. pass | 5. pass | 1. pass | 3. pass | 5. pass |
| Example 5 | 1.01 | 0.78 | 0.49 | −1.1 | −1.2 | 3.8 |
| Example 6 | 1.02 | 0.77 | 0.49 | −0.9 | 2.7 | 5.5 |
| Example 7 | 0.96 | 0.77 | 0.56 | 1.5 | 3.2 | 6.1 |
| Example 8 | 0.99 | 0.74 | 0.50 | 0.3 | 0.9 | 2.0 |
| Example 9 | 1.02 | 0.60 | 0.58 | 0.9 | 2.2 | 4.3 |
| Comp. ex. C | 0.92 | 0.66 | 0.45 | 1.8 | 2.4 | 3.0 |
| Comp. ex. E | 0.74 | 0.50 | 0.35 | 4.2 | 5.2 | 5.6 |

From the pellets of the pre-extrusion of Examples 5–9 approximately 150 μm cast film samples are prepared on a Reiffenhäuser extruder and exposed to artificial weathering in an Atlas Weather-O-Meter with a WOM 65 cycle (dry conditions).

The photooxidative degradation is followed by measuring the carbonyl Index (C=O-Index) by FT-IR-Spectroscopy and the mechanical properties (elongation at break (ELB) according to DIN 53455 after distinct periods.

The results can be seen in Table 3

TABLE 3

| Example | 200 h | 600 h | 1000 h | 1250 h | 1500 h |
|---|---|---|---|---|---|
| | C = O-Index after | | | | |
| Example 5 | 0.008 | 0.009 | 0.016 | 0.022 | 0.025 |
| Example 7 | 0.001 | 0.004 | 0.010 | 0.015 | 0.020 |
| Example 8 | 0.000 | 0.001 | 0.001 | 0.002 | 0.003 |
| Example 9 | 0.001 | 0.003 | 0.010 | 0.013 | 0.018 |
| Comp. ex. D | 0.007 | 0.025 | 0.044 | 0.054 | 0.066 |
| Comp. ex. E | 0.060 | >0.5 | | | |
| | retained elongation at break (%) after | | | | |
| Example 5 | 102 | 106 | 110 | 105 | 87 |
| Example 7 | 101 | 103 | 103 | 98 | 79 |
| Example 8 | 100 | 101 | 101 | 101 | 100 |
| Example 9 | 101 | 105 | 103 | 92 | 40 |
| Comp. ex. D | 106 | 103 | 80 | 58 | 31 |
| Comp. ex. E | 94 | 0 | | | |

Examples 10–12

In test vials, mixtures containing 98% of an acrylic powder coating material and 2% of the stabilizer listed below are dry blended and heated to 160° C. After 3 h and 6 h, turbidity and color change were determined.

Example 10 2,4-di-tert-butyl-phenyl-bis(1,2,2,6,6-pentamethylpiperdinyl)-phosphite;

Example 11 2,6-di-tert-butyl-4-methyl.phenyl-bis(1,2,2,6,6-pentamethylpiperdinyl)-phosphite;

Example 12 2,4,6-tri-tert-butyl-phenyl-bis(1,2,2,6,6-pentamethylpiperdinyl)-phosphite;

Comp. ex. F no additional stabilizer

The results can be seen in Table 4 below

TABLE 4

| Example | Turbidity 3 h/6 h | Color Change 3 h/6 h |
|---|---|---|
| Example 10 | none/none | trace yellow/trace yellow |
| Example 11 | none/none | none/none |
| Example 12 | none/none | none/none |
| Comp. ex. F | none/none | trace yellow/slight yellow |

What is claimed is:

1. A composition consisting essentially of:
   a) a compound containing a phosphite or phosphonite group and at least one 2,2,6,6-tetraalkylpiperidinyl group (herein defined as component a) of formulae:

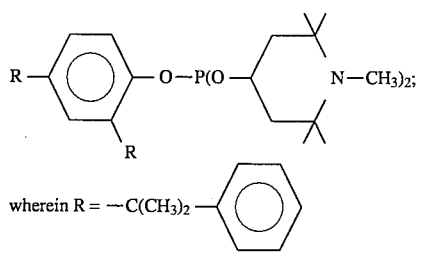

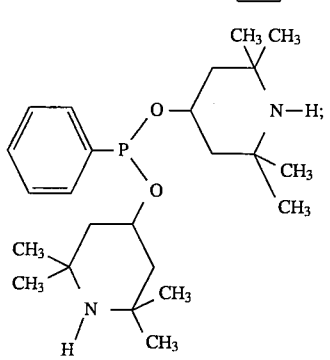

or

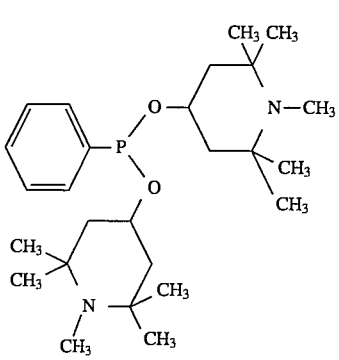

and b) a polyolefin which has been produced in the presence of a catalyst which is either
      i) a supported Ziegler catalyst or
      ii) a metallocene catalyst, from which polyolefin the catalyst has not been removed (hereinafter component b).

2. A composition according to claim 1 in which component a) is present in an amount of 0.01–5%, based on the weight of polyolefin present in the composition.

3. A composition according to claim 1 in which the polyolefins that can be stabilized are selected from polypropylene, polyethylene, polybutylene, poly-4-methylpentene, and copolymers thereof.

4. A composition comprising of a mixture consisting essentially of
   i) 1–90% of a phosphonite of formulae:

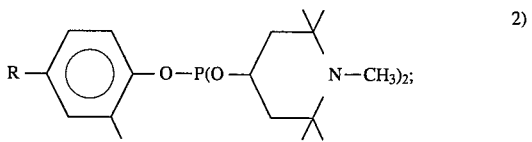

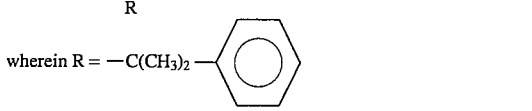

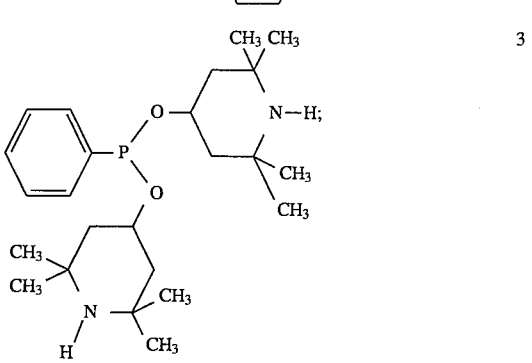

or

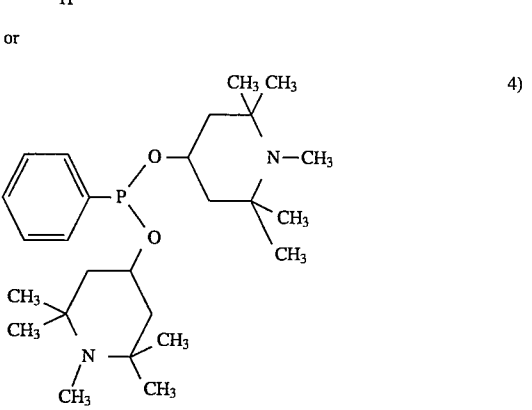

and ii) 99–10% of a phosphite of formula VIII (hereinafter defined as component ii):

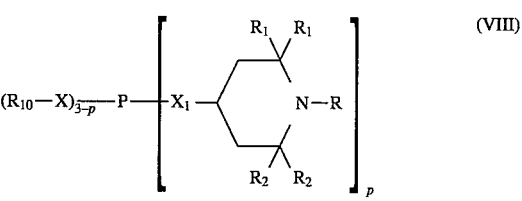

wherein:

R is hydrogen, oxygen, —OH, $C_{1-24}$alkyl, —O—$C_{1-24}$alkyl; —O—CO—$C_{1-24}$alkyl, —O—CO-phenyl, or —$COR_{15}$;

each $R_1$, independently, is —$CH_3$ or —$CH_2(C_{1-4}$alkyl) or both groups $R_1$ form a group —$(CH_2)_5$—;

each $R_2$ independently, is —$CH_3$ or —$CH_2(C_{1-4}$alkyl) or both groups $R_2$ form a group —$(CH_2)_5$—;

$R_3$ is hydrogen or $C_{1-4}$alkyl;

$R_7$ is hydrogen, $C_{1-12}$alkyl, $C_{5-6}$cycloalkyl, phenyl, phenyl—$C_{1-4}$alkyl, or $C_{1-12}$alkylphenyl;

$R_8$ is H or $C_{1-12}$alkyl;

$R_{10}$ is methyl, ethyl, linear or branched $C_{3-24}$alkyl, $C_{5-24}$cycloalkyl, $C_{7-24}$arylalkyl, or $C_{6-24}$aryl;

$R_{15}$ is —$C(R_3)$=$CH_2$, $C_{1-6}$alkyl, phenyl, —CO—$C_{1-24}$alkyl, —CO—phenyl, —$NR_7R_8$, —$CH_2$—$C_6H_5$, —CO—$OC_{1-12}$alkyl, or —COOH;

p is 1, 2, or 3; and $X_1$ is —O— or $N(R_3)$.

5. A method of stabilizing a polyolefin which has been produced in the presence of a catalyst which is either:
i) a supported Ziegler catalyst or
ii) a metallocene catalyst;
from which polyolefin the catalyst has not been removed which comprises incorporating into said polyolefin a stabilizing amount of a composition comprising: a)

a) a compound containing a phosphite or phosphonite group and at least one 2,2,6,6-tetraalkyipiperidinyl group (herein defined as component of formulae:

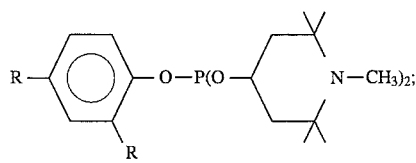
2)

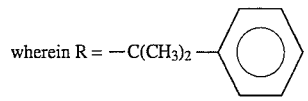

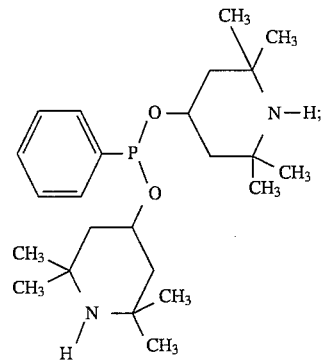
3 or

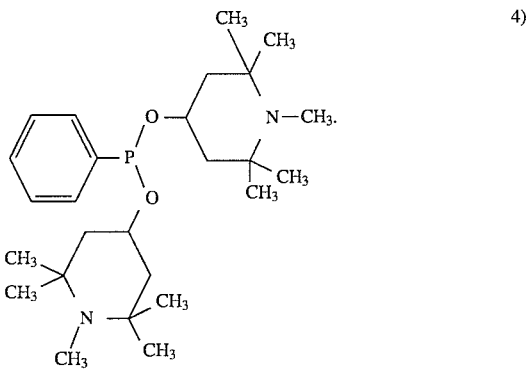
4)

6. A method of claim 5 in which component a) is present in an amount of 0.01–5%, based on the weight of polyolefin present in the composition.

7. A method of claim 6 in which the polyolefin is selected from polypropylene, polyethylene, polybutylene, poly-4-methylpentene, and coplymers thereof.

8. A compound of the formula XIII

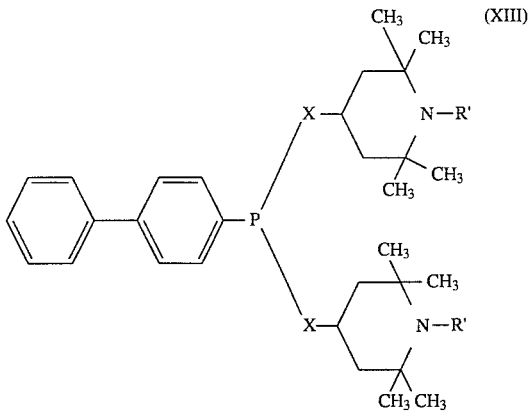
(XIII)

in which R' is hydrogen, —O—CO—phenyl, $C_{1-14}$alkyl, $C_{1-24}$alkoxy, —CO—$R_5'$ or —CO—CH=$CH_2$;

$R_5'$ is $C_{1-8}$alkyl, —$COC_{1-8}$alkyl, or —CO—O—$C_{1-4}$alkyl;

X is each independently a direct bond, —$N(R_3)$—, —O—, or —S—; and $R_3$ is H or $C_{1-4}$alkyl.

* * * * *